US009689804B2

(12) United States Patent
Bobrov

(10) Patent No.: US 9,689,804 B2
(45) Date of Patent: Jun. 27, 2017

(54) MULTI-CHANNEL BACKSIDE WAFER INSPECTION

(71) Applicant: KLA-Tencor Corporation, Milpitas, CA (US)

(72) Inventor: Yakov Bobrov, Burlingame, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 55 days.

(21) Appl. No.: 14/577,374

(22) Filed: Dec. 19, 2014

(65) Prior Publication Data

US 2015/0233841 A1  Aug. 20, 2015

Related U.S. Application Data

(60) Provisional application No. 61/920,458, filed on Dec. 23, 2013.

(51) Int. Cl.
*G01B 11/24* (2006.01)
*G01N 21/88* (2006.01)
(Continued)

(52) U.S. Cl.
CPC ......... *G01N 21/8806* (2013.01); *G01B 11/24* (2013.01); *G01N 21/9501* (2013.01);
(Continued)

(58) Field of Classification Search
USPC .... 356/237.1–241.6, 242.1–243.8, 426–431, 356/600–640
See application file for complete search history.

(56) References Cited

U.S. PATENT DOCUMENTS 4,319,270 A * 3/1982 Kimura ................. G01N 25/72
250/559.46
4,577,095 A * 3/1986 Watanabe ............ G03F 9/7026
250/201.2
(Continued)

FOREIGN PATENT DOCUMENTS

EP          0898300 B1    11/2005
EP          1601995 A2    12/2005
JP        2001-134760 A    5/2001

OTHER PUBLICATIONS

PCT Search Report, Application No. PCT/US2014/072211, Mail date Mar. 31, 2015, 3 pages.

*Primary Examiner* — Tri Ton
*Assistant Examiner* — Jarreas C Underwood
(74) *Attorney, Agent, or Firm* — Suiter Swantz pc llo

(57) ABSTRACT

A system for inspecting a backside surface of a wafer with multi-channel focus control includes a set of inspection sub-systems including a first inspection sub-system positioned and an additional inspection sub-system. The first and additional inspection sub-systems include an optical assembly, an actuation assembly, where the optical assembly is disposed on the actuation assembly, and a positional sensor configured to sense a position characteristic between a portion of the optical assembly and the backside surface of the wafer. The system also includes a controller configured to acquire one or more wafer profile maps of the backside surface of the wafer and adjust a first focus position of the first inspection sub-system or an additional focus position of the additional inspection sub-system based on the received one or more wafer profile maps.

22 Claims, 11 Drawing Sheets

(51) Int. Cl.
  *G01N 21/95* (2006.01)
  *H01L 21/66* (2006.01)
(52) U.S. Cl.
  CPC .......... *H01L 22/12* (2013.01); *G01N 2201/02* (2013.01); *G01N 2201/06113* (2013.01)

(56) References Cited

U.S. PATENT DOCUMENTS

| | | | |
|---|---|---|---|
| 5,159,202 A * | 10/1992 | Ametani | H01L 21/681 250/559.22 |
| 6,294,793 B1 * | 9/2001 | Brunfeld | G01N 21/9506 250/559.45 |
| 6,544,802 B1 * | 4/2003 | Jun | H01L 21/67288 438/14 |
| 6,791,680 B1 * | 9/2004 | Rosengaus | G01N 21/9501 356/237.2 |
| 6,801,650 B1 * | 10/2004 | Kikuchi | G01N 21/956 250/201.4 |
| 6,879,167 B2 * | 4/2005 | Ju | G01N 22/02 324/637 |
| 7,015,418 B2 | 3/2006 | Cahill | |
| 7,354,779 B2 * | 4/2008 | Brodsky | H01L 21/0271 257/E21.024 |
| 7,411,385 B2 * | 8/2008 | Kirchdoerffer | H03K 17/9505 324/207.15 |
| 7,508,504 B2 | 3/2009 | Forderhase et al. | |
| 7,571,422 B2 * | 8/2009 | Adel | G03F 7/70633 716/51 |
| 7,629,798 B2 * | 12/2009 | Mallory | H01L 21/67265 324/686 |
| 7,724,357 B2 | 5/2010 | Smedt | |
| 7,919,760 B2 | 4/2011 | Jau et al. | |
| 8,224,062 B2 | 7/2012 | Fukuda et al. | |
| 8,410,460 B2 | 4/2013 | Yoshida | |
| 8,778,572 B2 * | 7/2014 | Fukuhara | G03F 1/26 430/5 |
| 2006/0243711 A1 | 11/2006 | Paradis et al. | |
| 2009/0030639 A1 | 1/2009 | Czerkas | |
| 2009/0122304 A1 * | 5/2009 | Jin | G01N 21/9503 356/237.4 |
| 2013/0271596 A1 | 10/2013 | Lewis et al. | |

* cited by examiner

MULTI-CHANNEL BACKSIDE WAFER INSPECTION

CROSS-REFERENCE TO RELATED APPLICATION

The present application claims the benefit under 35 U.S.C. §119(e) of U.S. Provisional Application Ser. No. 61/920,458, filed Dec. 23, 2013, entitled SAMPLE INSPECTION AND REVIEW IN SEMICONDUCTOR FABRICATION OR TESTING, naming Yakov Bobrov as an inventor, which is incorporated herein by reference in the entirety.

TECHNICAL FIELD

The present invention generally relates to sample inspection and review and, in particular, to backside semiconductor wafer review during semiconductor device testing and fabrication.

BACKGROUND

As tolerances on semiconductor device fabrication processes continue to narrow, the demand for improved semiconductor wafer inspection and review tools continues to increase. One such review tool includes a wafer inspection tool, such as a backside wafer inspection tool. While most front-side inspection systems utilize a chuck, such as a vacuum chuck, or other means of securing the wafer flat, a backside inspection system requires the wafer to be secured in an unrestrained state. This presents challenges for optical systems where depth of focus is limited. In such backside inspection systems, a semiconductor wafer is typically supported at the edge either by a continuous line of contact or at several discrete points, with the wafer behaving as a free membrane. As a result, the wafer displays a significant amount of "sag" due to gravity or additional "warp" caused by stress associated with the surface tension of one or more thin film coatings deposited on the wafer. Typical approaches, such as single channel optical systems, suffer from limited throughout. In addition, prior multi-channel systems merely provide global focus correction, limiting the ability to correct for sag and warp in a given wafer. Therefore, it would be advantageous to provide a system and method that cures the defects identified in the previous art.

BRIEF DESCRIPTION OF THE DRAWINGS

The numerous advantages of the disclosure may be better understood by those skilled in the art by reference to the accompanying figures in which:

FIG. 1O illustrates a process flow diagram depicting a method for adjusting a focus of a single inspection channel in the multi-channel system, in accordance with one or more embodiments of the present disclosure.

DETAILED DESCRIPTION OF THE INVENTION

Reference will now be made in detail to the subject matter disclosed, which is illustrated in the accompanying drawings.

Figure 1A:
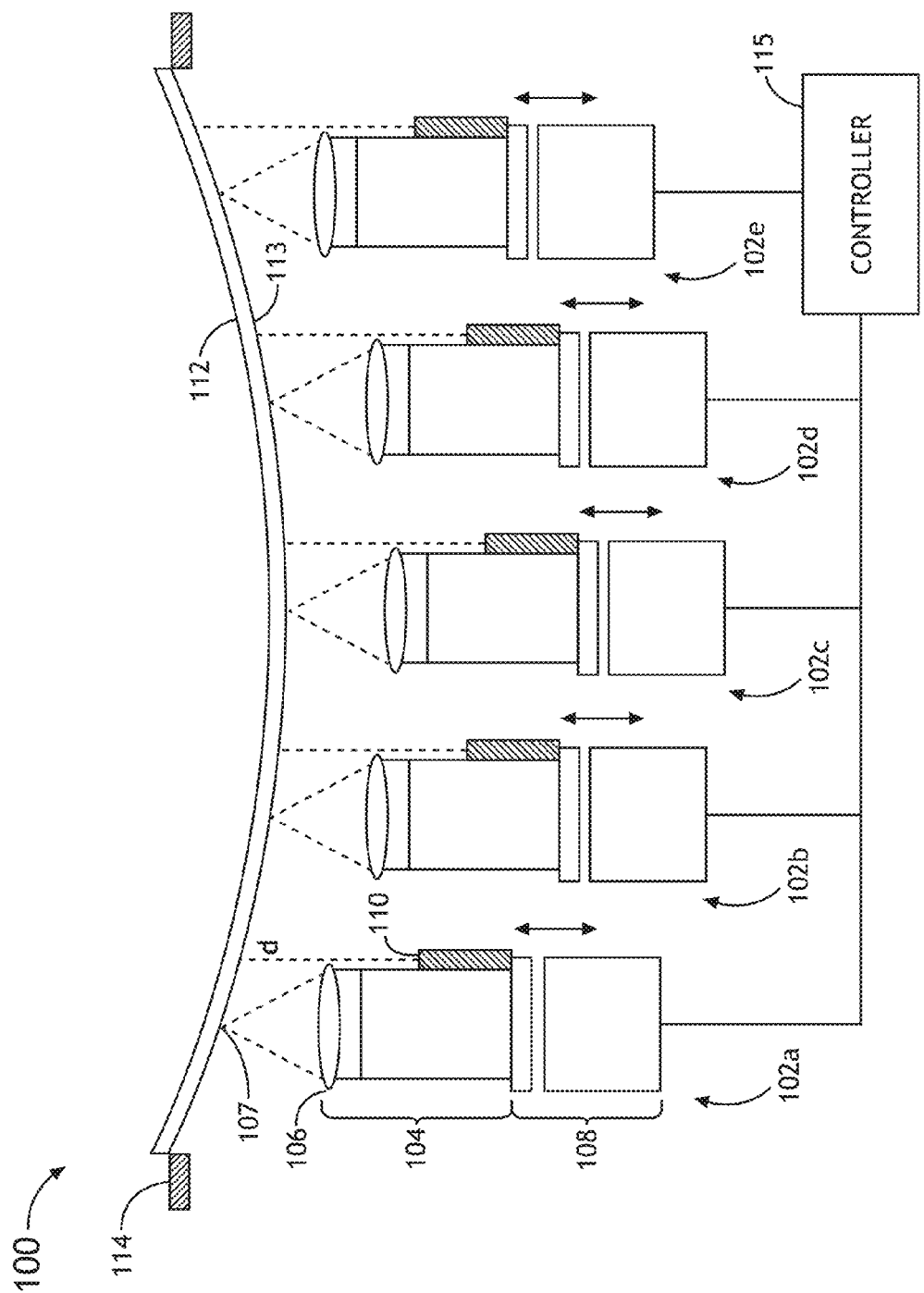
FIG. 1A illustrates a simplified schematic view of a multi-channel inspection system with individual channel focus control, in accordance with one or more embodiments of the present disclosure.

Referring generally to FIGS. 1A through 1O, a system and method for inspect a backside surface of a wafer is disclosed.

Embodiments of the present disclosure are directed to methods and systems for individually focusing single inspection channels of a multi-channel backside wafer inspection system.

Embodiments of the present disclosure are suitable for performing an inspection or review measurement process on a wafer constrained at the edge of the wafer via a line of contact or a number of discrete contact points. In this regard, embodiments of the present disclosure may serve to inspect or review one or more wafers displaying gravitation sag and/or film induced warp.

Embodiments of the present disclosure an inspection including two or more inspection channels, where each channel is independently capable of focus adjustment. The focus adjustment imparted to a given inspection channel of the multi-channel system may be based on the shape of the wafer in an un-chucked state. Embodiments of the present disclosure allow for the focus of each individual channel to be automatically adjusted as the wafer and the components of the multi-channel inspection channel move with respect to each other. The focus of each inspection channel may be adjusted via an individual actuator dedicated to a particular inspection channel. Some embodiments of the present disclosure provide a focus adjustment of individual inspection channels using previously performed wafer profile mapping data (i.e., pre-mapping). Some embodiments of the present disclosure provide a focus adjustment of individual inspection channels using wafer shape data obtained with an independent wafer shape measurement device. Some embodiments of the present disclosure provide real-focus adjustment of individual inspection channels using a real-time (or near real-time) focus measurement device (e.g., auto-focus device).

It is noted that the various embodiments of the present disclosure may provide improved throughput and improved repeatability of inspection results.

FIG. 1A illustrates a simplified schematic view of a multi-channel inspection system 100 with individual channel focus control, in accordance with one or more embodiments of the present disclosure.

In one embodiment, the system 100 includes a set of inspections sub-systems 102a-102e. For example, each of the inspection sub-systems 102a-102e may be located at a different wafer position such that multiple areas of the wafer 112 may be scanned or imaged simultaneously. In another embodiment, the inspection sub-systems 102a-102e are configured to scan and/or image backside of the wafer 112, which is secured via one or more contacts 114. As noted, due to the un-restrained state of the wafer 112, the wafer 112 displays a significant amount of sag due to gravity and/or warp caused by the surface tension of one or more thin film layers deposited on the wafer 112. For example, in the case of a 450 mm wafer, the sag and warp of the wafer 112 may exceed 1 mm. In another embodiment, at any given instant, each inspection may be located at different lateral positions (e.g., X-Y positions) across the backside surface 113 of the wafer 112. It is noted that as the wafer 112 is scanned above the inspection sub-systems 102a-102e (or the inspection sub-systems 102a-102e are scanned across the wafer) the sag and/or warp of the wafer 112 causes the focal point 107 of the light from a particular inspection sub-system 102a-102e to become misaligned with the wafer surface 113, resulting in less than ideal focus for the associated imagery/inspection data for the particular channel (see FIGS. 1E-1F). The remainder of the present disclosure describes a variety of embodiments suitable for correcting the focus of the individual inspection channels 102a-102e.

In one embodiment, each inspection sub-system 102a-102e includes an optical assembly 104. In another embodiment, each inspection sub-system 102a-102e includes one or more positional sensors 110. In one embodiment one or more of the positional sensors 110 are configured to sense a position characteristic between a portion of the particular optical assembly 104 and the backside surface 113 of the wafer 112. The position characteristic may include any parameter known in the art related to positioning and alignment of wafers. For example, the position characteristic may include, but is not limited to, distance, change in distance, velocity and the like. For instance, a particular position sensor may measure the distance, d, between the portion of an inspection sub-system 102a-102e (e.g., portion of optical assembly 104) and the surface 113 of the wafer 112. It is noted herein that the position sensors 110 of system 100 may include any position, height or focus sensor known in the art.

In another embodiment, the each inspection sub-system 102a-102e includes an actuation assembly 108. In one embodiment, the optical assembly 104 of a given inspection sub-system 102a-102e and the corresponding position sensor 110 are selectively actuated by the actuation assembly 108. For example, as discussed further herein, the actuation assembly 108 of a particular inspection sub-system 102a-102e may serve to adjust the position of the optical assembly 104 and, thus, the focus position 107 of the illumination from the inspection sub-system 102a-102e. Such an adjustment may be made in response to a measured changed in the distance, for example, between the optical assembly 104 and the surface 113 of the wafer 112. In one embodiment, the actuation assembly 108 may include an actuation stage 109 and an actuator 111. In this regard, the actuator 111 may translate the actuation stage 109 (and one or more portion of the optical assembly 104 and the sensor 110) by a selected distance.

Figure 1B:
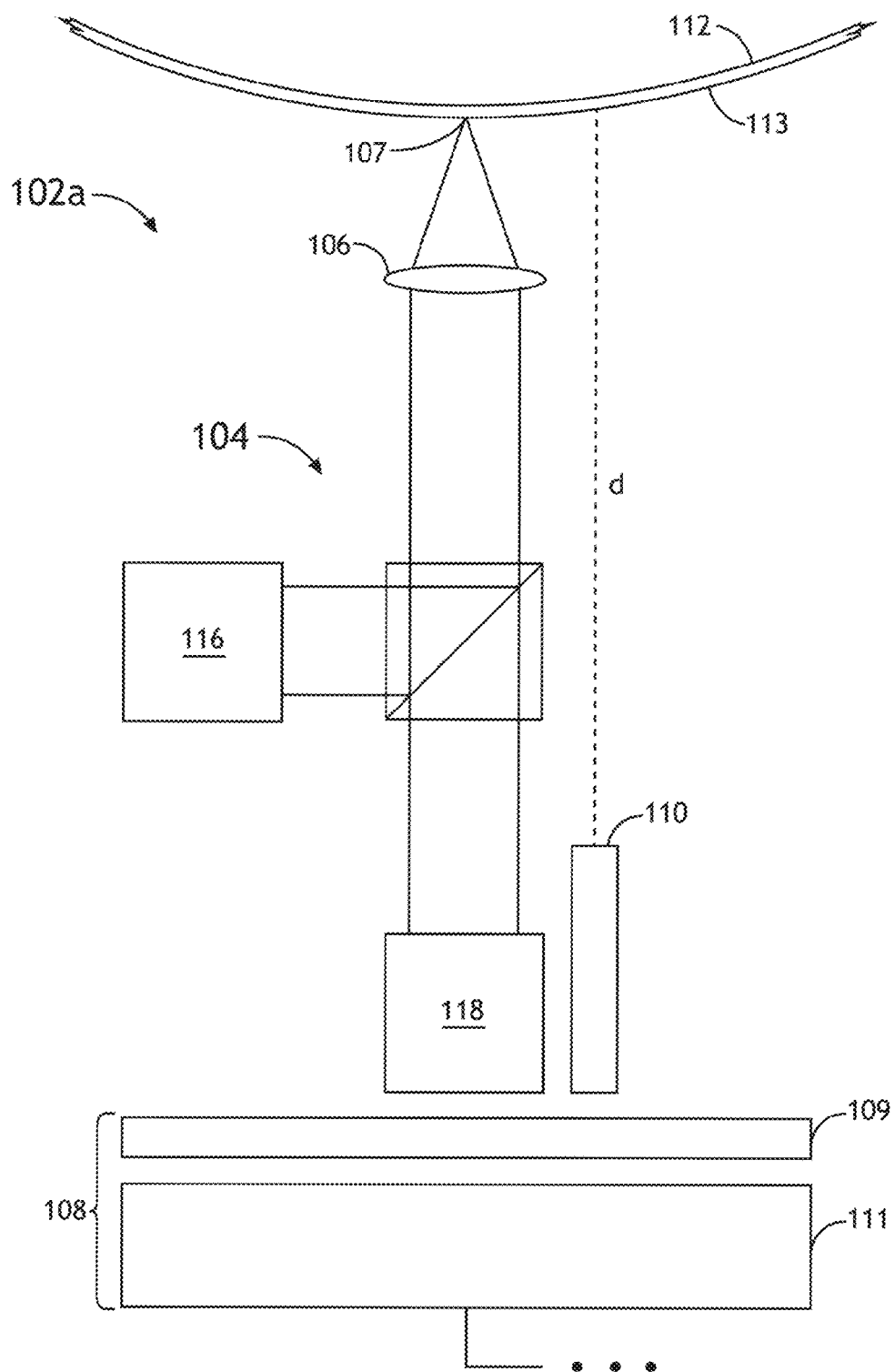
FIG. 1B illustrates a simplified schematic view of a single inspection sub-system of the multi-channel inspection system, in accordance with one embodiment of the present disclosure.

FIG. 1B illustrates a simplified schematic view of a single inspection sub-system 102a of the multi-channel inspection system 100, in accordance with one embodiment of the present disclosure. It is noted that the various embodiments and components of the single inspection sub-system 102a depicted in FIG. 1B may be extended to each (or at least some) of the inspection sub-systems (e.g., 102b-102e) of the inspection system 100.

In one embodiment, inspection sub-system 102a includes an optical assembly 104. The optical assembly 104 may include any set of optical elements or components known in the art necessary to perform an inspection process on the wafer 112. In one embodiment, the optical assembly 104 includes an objective lens 106 arranged to focus light from the illumination source 116 to a focal point 107 on the backside surface 113 of the wafer 112. The illumination source 116 may include any illumination source known in the art suitable for use in a wafer inspection system. For example, the illumination source 116 may include, but is not limited to, one or more narrowband sources (e.g., laser source). By way of another example, the illumination source 116 may include, but is not limited to, one or more broadband sources (e.g., lamp source).

In another embodiment, the optical assembly 104 includes a detector 118 arranged to collect light reflected, scatter or diffracted from the backside surface 113 of the wafer 112. The detector 118 may include any detector known in the art suitable for use in wafer inspection. For example, the detector 118 may include, but is not limited to, a CCD detector, a TDI-CCD detector, a PMT tube and the like.

It is noted herein that the optical assembly 104 of the inspection sub-system 102a may include any number of additional or alternative optical elements or components and the inspection sub-system 102a is not limited to the components depicted in FIG. 1B. For example, the optical assembly 104 may include, but is not limited to, one or more additional illumination optics (e.g., lenses, filters, steering elements and the like). By way of another example, the optical assembly 104 may include, but is not limited to, one or more additional collection optics (e.g., lenses, filters, steering elements and the like). It is further noted herein that the optical assembly 104 of the inspection sub-system 102a may be configured to perform brightfield wafer inspection or darkfield wafer inspection. The optical assembly 104 may also be performed to carry out imaging-mode inspection or scanning-mode inspection.

In another embodiment, the system 100 includes one or more controllers 115. In one embodiment, the controller 115 is communicatively coupled to each of the actuation assemblies 108 and each of the position sensors 110. In one embodiment, the controller 115 may direct the actuation assembly 108 of a particular inspection sub-system 102a-102e to adjust the associated focus position 107 by controlling the position of the respective optical assembly 104. An adjustment to a particular focus position 107 may be made in response to a measured changed in the distance, for example, between the optical assembly 104 and the surface 113 of the wafer 112 received by the controller 115 from the respective position sensor 110.

In one embodiment, the controller 115 is configured to acquire one or more wafer profile maps of the backside surface 113 of the wafer 112. In another embodiment, the controller 115 is configured to adjust the focus positions associated with the inspection sub-system 102a-102e based on the received one or more wafer profile maps.

In one embodiment, the controller 115 of system 100 includes one or more processors (not shown) configured to execute program instructions stored on a memory medium (not shown). In this regard, the one or more processors of controller 115 may carry out any of the various process steps of the present disclosure.

Figure 1C:
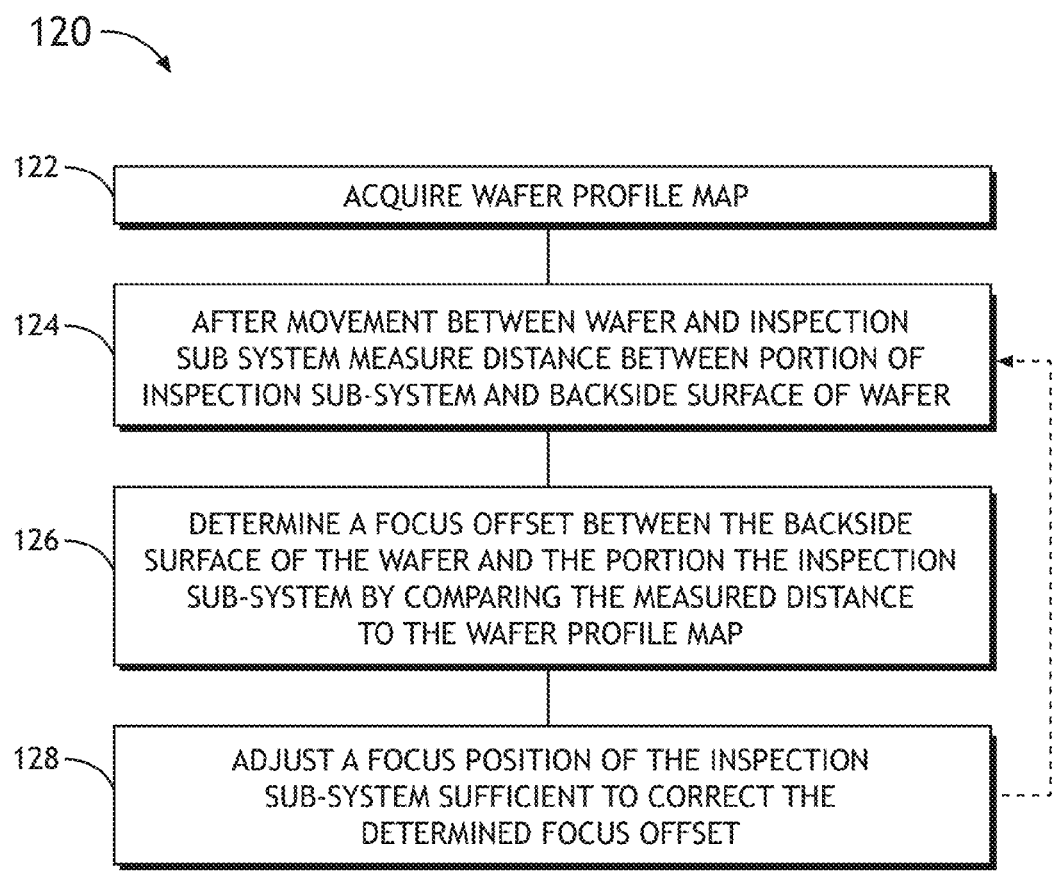
FIG. 1C illustrates a process flow diagram depicting a method for adjusting a focus of a single inspection channel in the multi-channel system, in accordance with one or more embodiments of the present disclosure.

FIG. 1C illustrates a process flow diagram depicting a method 120 for adjusting a focus of a single inspection channel in the multi-channel system 100, in accordance with one or more embodiments of the present disclosure.

Figure 1D:
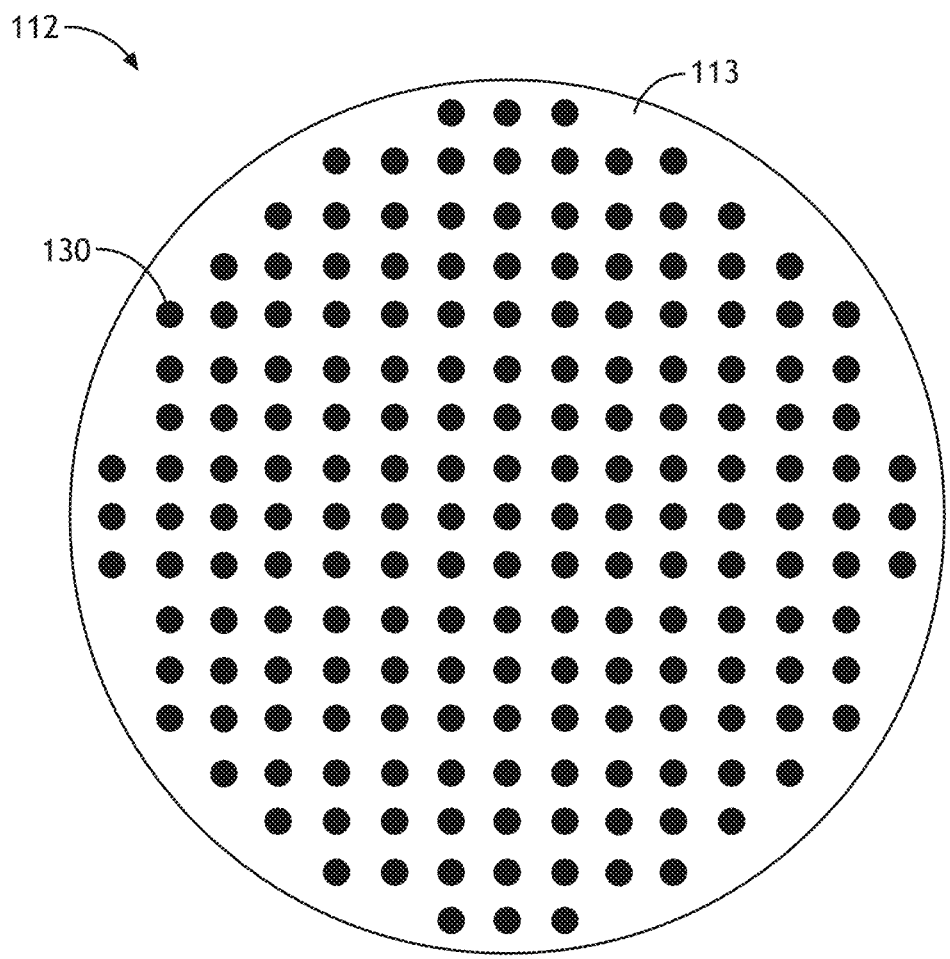
FIG. 1D illustrates a conceptual view of a wafer profile map acquired prior to one or more inspection scanning processes.

In step 122, the controller 115 may acquire one or more wafer profile maps. In one embodiment, the system 100 may perform a pre-scan and/or pre-mapping process on the backside surface 113 of wafer 112 in order to acquire one or more wafer profile maps. In one embodiment, one or more of the positional sensors 110 of the respective inspection sub-systems 102a-102e may be used to perform a pre-scan and/or pre-mapping process on the backside surface 113 of wafer 112 in order to acquire one or more wafer profile maps. For example, as shown in FIG. 1D, a wafer profile map 130 may be generated by measuring a position characteristic, such as distance or height, at a number of positions across the backside surface 113 of the wafer 112. In this regard, the measured position characteristic, such as distance from the one or more sensors 110 and the surface 113, at each measurement location 132 may be aggregated to form the wafer profile map 130, as conceptually illustrated in FIG. 1D. It is noted that the one or more wafer profile maps acquired during the pre-mapping process may then serve as reference for focus adjust during the given inspection scanning process. In another embodiment, following measurement of one or more position characteristics with the one or more positional sensors 110, the one or more position sensors 110 may transmit the acquired position characteristic data to the controller 115. In turn, the controller 115 may generate the associated wafer profile map.

Figure 1E:
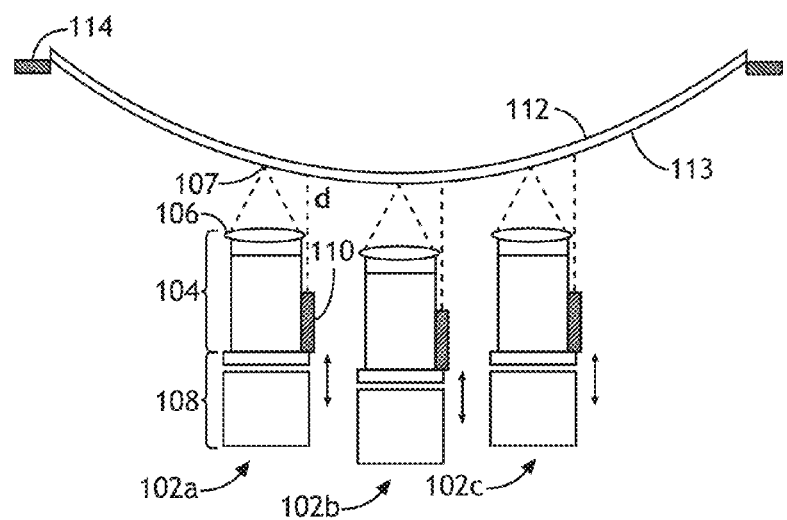
FIGS. 1E-1G illustrate a conceptual view of a focus adjustment of the inspection sub-systems of the multi-channel inspection system, in accordance with one or more embodiments of the present disclosure.

For example, FIG. 1E depicts the measurement of the distance between each of the inspection sub-systems 102a-102c in a well-focused state, with the focal point 107 being aligned with the backside surface 113 of the wafer. Such a configuration may represent the pre-mapping performed prior to a given inspection scan of the wafer 112. As shown in FIG. 1E, the distance between any particular position sensor 110 and the backside surface of the wafer 112 may be represented by d.

In another embodiment, one or more wafer shape measurement systems may be used to perform a pre-scan and/or pre-mapping process on the backside surface 113 of wafer 112 in order to acquire one or more wafer profile maps. In one embodiment, the wafer shape measurement system used to perform the pre-mapping process may include an external wafer shape measurement system (e.g., see wafer shape measurement system 140 of FIG. 1J). For example, the wafer shape measurement system may include any measurement system known in the art used to characterize the shape of a backside surface of a wafer. For instance, the wafer shape measurement system may include, but is not limited to, an optical-based wafer shape measurement system, a proximity-based wafer shape measurement system, an inductance-based wafer shape measurement system or an air-pressure-based wafer shape measurement system. In this regard, the wafer profile map 130 may be generated by measuring a position characteristic, such as distance or height, at a number of positions across the backside surface 113 of the wafer 112 using the external wafer shape measurement system. In another embodiment, following measurement of one or more position characteristics with the wafer shape measurement system, the wafer shape measurement system may transmit the acquired position characteristic data to the controller 115. In turn, the controller 115 may generate the associated wafer profile map.

In step 124, the position sensor 110 of a particular inspection sub-system 102a-102e may measure the distance between a portion of the particular inspection sub-system and the backside surface 113 of the wafer 112.

Figure 1F:
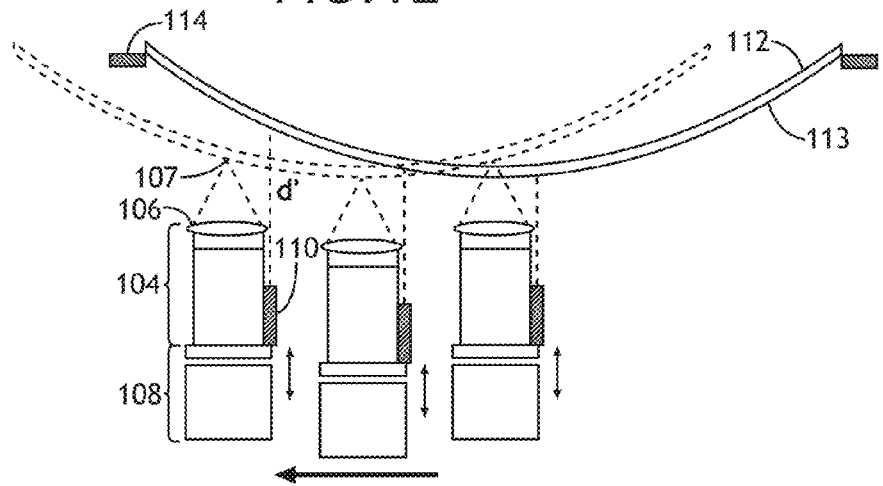

As shown in FIG. 1F, after a relative movement between the wafer 112 and set of inspection sub-systems 102a-102c, some of the inspection sub-systems 102a-102c become out of focus due to the sag and/or warp of the wafer 112. As such, following a relative lateral movement between the wafer 112 and the inspection sub-systems 102-102c, the one or more position sensors 110 may measure the distance between a portion of the particular inspection sub-system and the backside surface 113 of the wafer 112. As shown in FIG. 1F, the distance between any particular position sensor 110 (or any other portion of the inspection sub-system) and the backside surface of the wafer 112, when the given inspection sub-system is in an out-of-focus state, may be represented by d'. In another embodiment, following measurement of one or more position characteristics with the wafer shape measurement system, the wafer shape measurement system may transmit the acquired position characteristic data to the controller 115.

In step 126, the controller 115 may determine a focus offset, at a given wafer position, between the backside surface 113 of the wafer 112 and the portion of the particular inspection sub-system 102a-102e. In one embodiment, the focus offset between the backside surface 113 of the wafer 112 and the portion of the particular inspection sub-system 102a-102e is determined by comparing the measured distance of step 124 to data of the wafer profile map at the same wafer position, as provided in step 122.

Figure 1G:
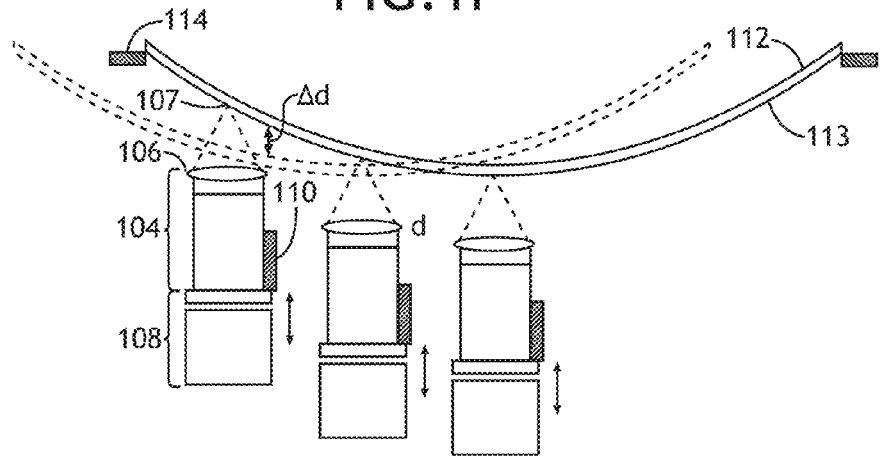

In step 128, the controller 115 may direct the actuation assembly 108 to adjust the focus position 107 of the inspection sub-system to a degree sufficient to correct for the determined focus offset, equal to or related to Δd, as shown in FIG. 1G. Here, Δd is related to the distance d and the distance d' by:

$$\Delta d = d - d'$$

It is noted that the measurements of distance above may be relative to a respective position sensor 110 of a give inspection sub-system 102a-102c or any other reference point within the given inspection sub-system 102a-102c.

Further, due to possibility of lateral separation between the position sensor 110 and the focus 107, the measured Δd with the respect to distance between the position sensor 110 and wafer surface 113 is not necessarily equal to the distance needed for focus offset correction. As such, the distance needed for focus offset correction may be estimated using the Δd value and the curvature, or an estimation of the effects of curvature, of the wafer 112. In another embodiment, the position sensor 110 may be positioned such that it is closely aligned with the focal point 107 so that illumination from the position sensor 110 used for measuring position strikes the wafer 112 at approximately the same lateral position as the focal point 107.

In one embodiment, the actuation assembly 108 may translate any portion of the optical assembly 104 in order to adjust the focus position 107 of the illumination sub-system. In one embodiment, the actuation assembly 108 may translate the entire optical assembly 104 in order to translate the focal point 107 relative to the surface 113 of the wafer 112. In another embodiment, the actuation assembly 108 may translate a selected portion of the optical assembly 104 in order to translate the focal point 107 relative to the surface 113 of the wafer 112. For example, the actuation assembly 108 may be positioned such that it may independently translates the objective 106 (or any additional focusing element of the optical assembly 104) in order to translate the focal point 107 relative to the surface 113 of the wafer 112.

Figure 1H:
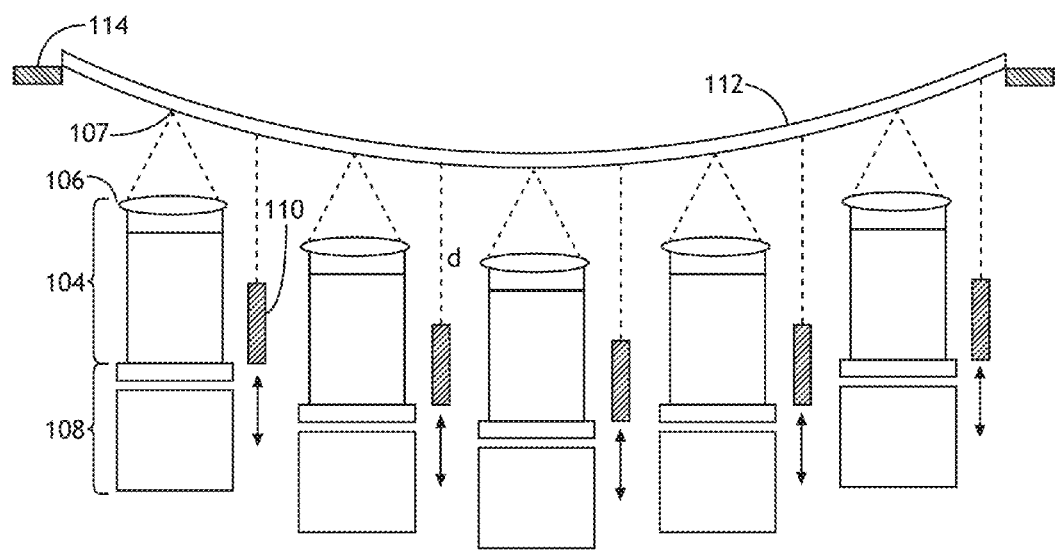
FIG. 1H illustrates a simplified schematic view of a multi-channel inspection system with vertically fixed position sensors, in accordance with one or more embodiments of the present disclosure.
Figure 1I:
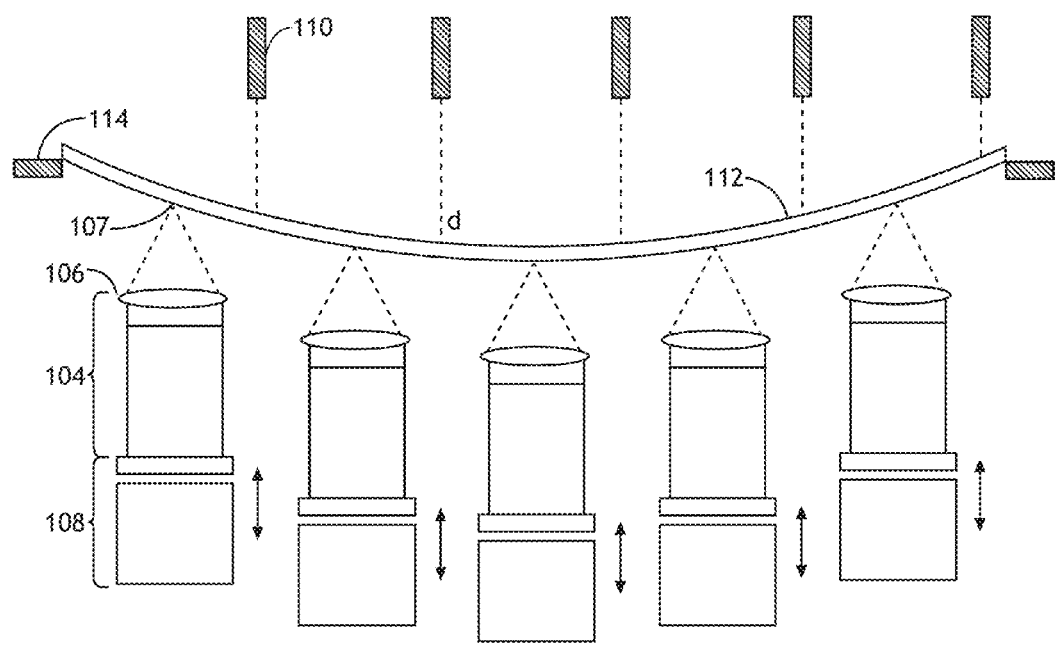
FIG. 1I illustrates a simplified schematic view of a multi-channel inspection system with position sensors positioned at the front-surface of the wafer, in accordance with one or more embodiments of the present disclosure.

While the various figures of the present disclosure depict the one or more position sensors 110 as being located proximate to the optical assembly 104 of the respective inspection sub-systems 102a-102c, this should not be interpreted as a limitation. It is recognized herein that the position sensors may be located at a variety of locations within system 100. For example, as shown in FIG. 1G, one or position sensors 110 may be coupled to an assembly (not shown) located between the inspection sub-systems 102a-102e such that the one or more position sensors are not vertically translated by the actuation assembly 108, but may be laterally translated by the assembly securing the group of inspection sub-systems 102a-102e during scanning. By way of another example, as shown in FIG. 1H, one or more of the position sensors 110 may be located at the front-surface of the wafer 112.

Figure 1J:
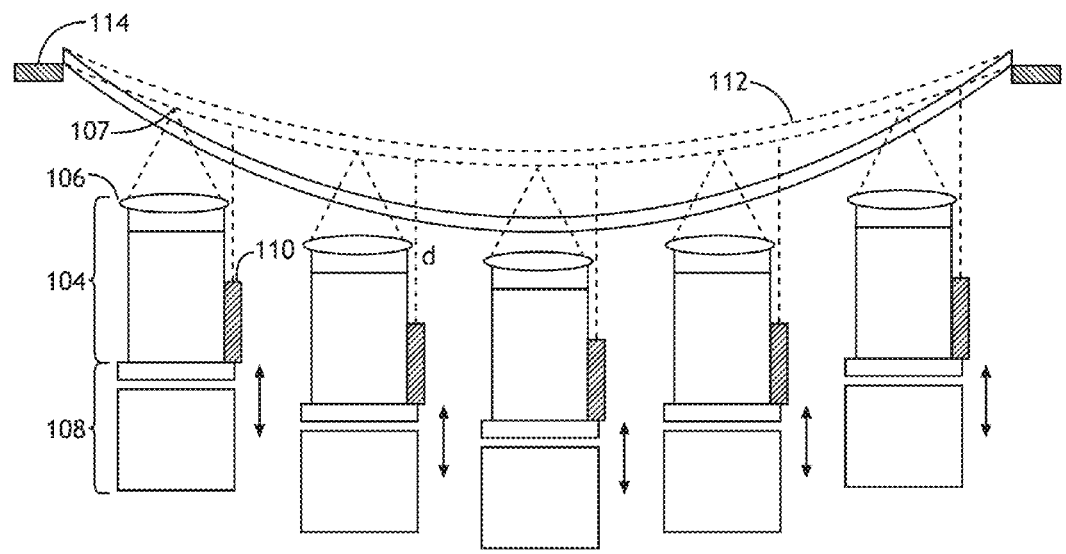
FIGS. 1J-1K illustrates a simplified schematic view of a multi-channel inspection system with individual channel focus control in a setting with a change in wafer shape, in accordance with one or more embodiments of the present disclosure.
Figure 1K:
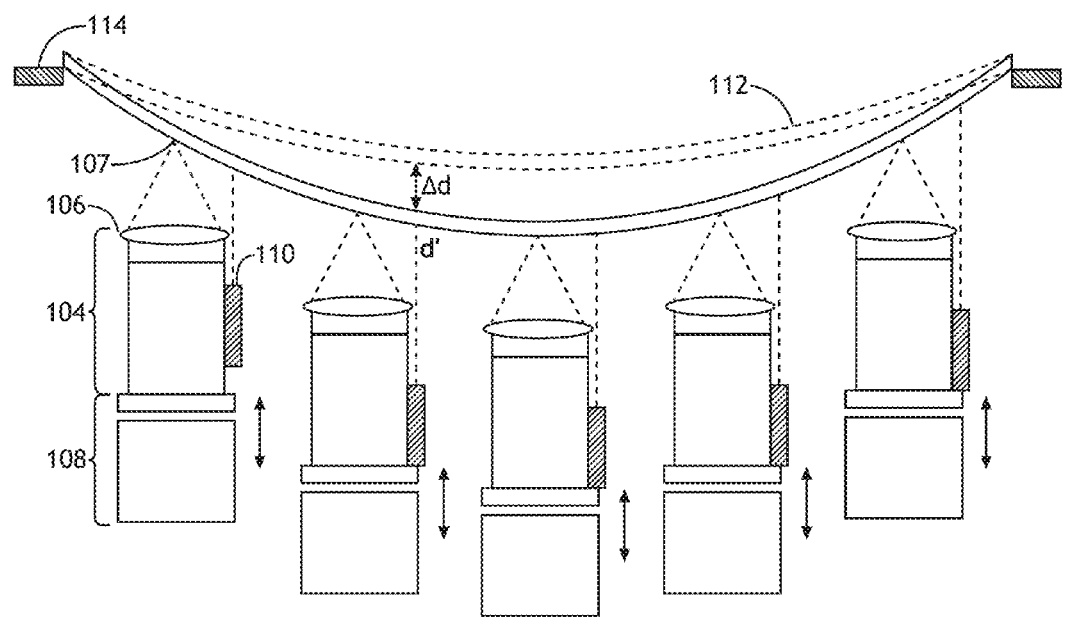

FIGS. 1J and 1K illustrate a simplified schematic view of the multi-channel inspection system 100 arranged to provide focus adjustment in settings where the backside surface 113 of the wafer 112 changes shape and/or position. For example, due to changes in warp, the surface profile of the wafer 112 may be altered. Similar to the case where the quality of focus was reduced by the motion of the wafer/inspection sub-systems 102a-102e, a change in wafer profile may also cause a reduction in the quality of focus of a given inspection channel. It is noted herein that the process(es) described previously herein may be extended to the embodiment depicted in FIGS. 1J and 1K to adjust focus of the inspection sub-systems 102a-102e following a change in the wafer shape profile.

Figure 1L:
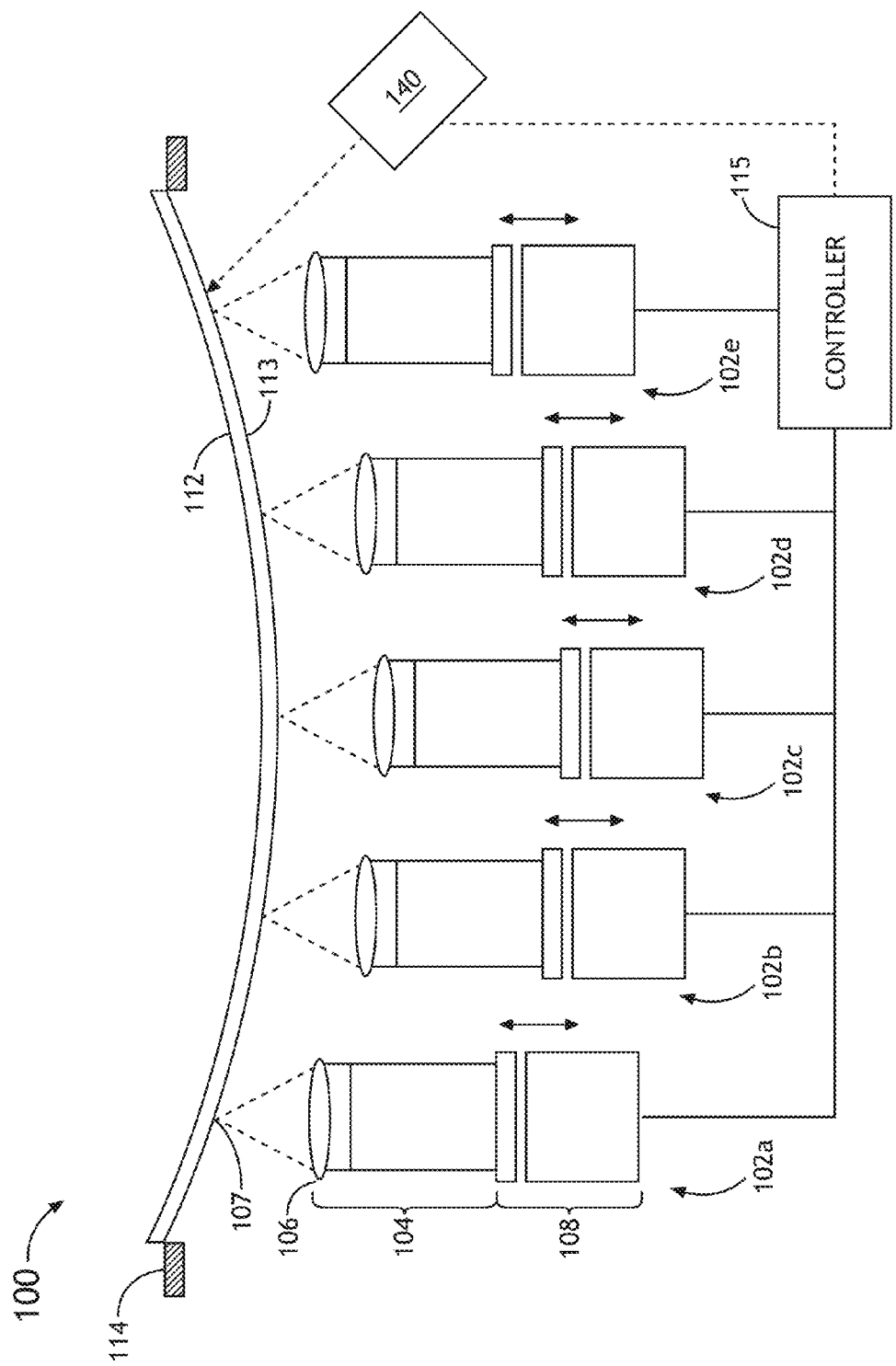
FIG. 1L illustrates a simplified schematic view of a multi-channel inspection system with individual channel focus control where wafer surface position is monitored with a wafer shape measurement system, in accordance with one or more embodiments of the present disclosure.

FIG. 1L illustrates a simplified schematic view of a multi-channel inspection system with individual channel focus control where wafer surface position is monitored with a wafer shape measurement system, in accordance with one or more embodiments of the present disclosure.

In one embodiment, the system 100 includes one or more wafer shape measurement systems 140. It is noted herein that the depiction of the wafer shape measurement system 140 is not limiting and is provided merely for illustrative purposes. It is recognized herein that the system 100 may include any number of wafer shape measurement systems. Further, the wafer shape system 140 may further be positioned on the frontside of the wafer 112 in order to collect wafer shape data. It is noted that wafer shape data of any form may be suitable for use in the system 100, provided the shape of the wafer 112 at a given lateral position is correlated with the lateral position of the inspection sub-systems 102a-102e.

In one embodiment, the one or more wafer shape measurement systems 140 are communicatively coupled to the controller 115.

In one embodiment, the controller 115 is configured to acquire wafer shape data from the wafer shape measurement system 140. For example, the wafer shape data from the wafer shape measurement system 140 may correspond to wafer position, height or profile data corresponding with a wafer position of one or more of the respective inspection sub-systems 102a-102e. In another embodiment, the controller 115 is further configured to adjust a focus position of one or more of the respective inspection sub-systems 102a-102e based on the wafer shape data from the wafer shape measurement system 140. In this regard, the various processes and components described previously herein with respect to FIGS. 1A-1 should be interpreted to extend to the embodiment of FIG. 1L. Further, the processes used to carry out a focus offset procedure should also be interpreted to extend to FIG. 1L.

It is noted herein that the wafer shape measurement system 140 may include any wafer shape measurement system or tool known in the art. For example, the one or more wafer shape measurement system may include, but is not limited to, at least one of an optical-based wafer shape measurement system, a proximity-based wafer shape measurement system, an inductance-based wafer shape measurement system or an air-pressure-based wafer shape measurement system.

Figure 1M:
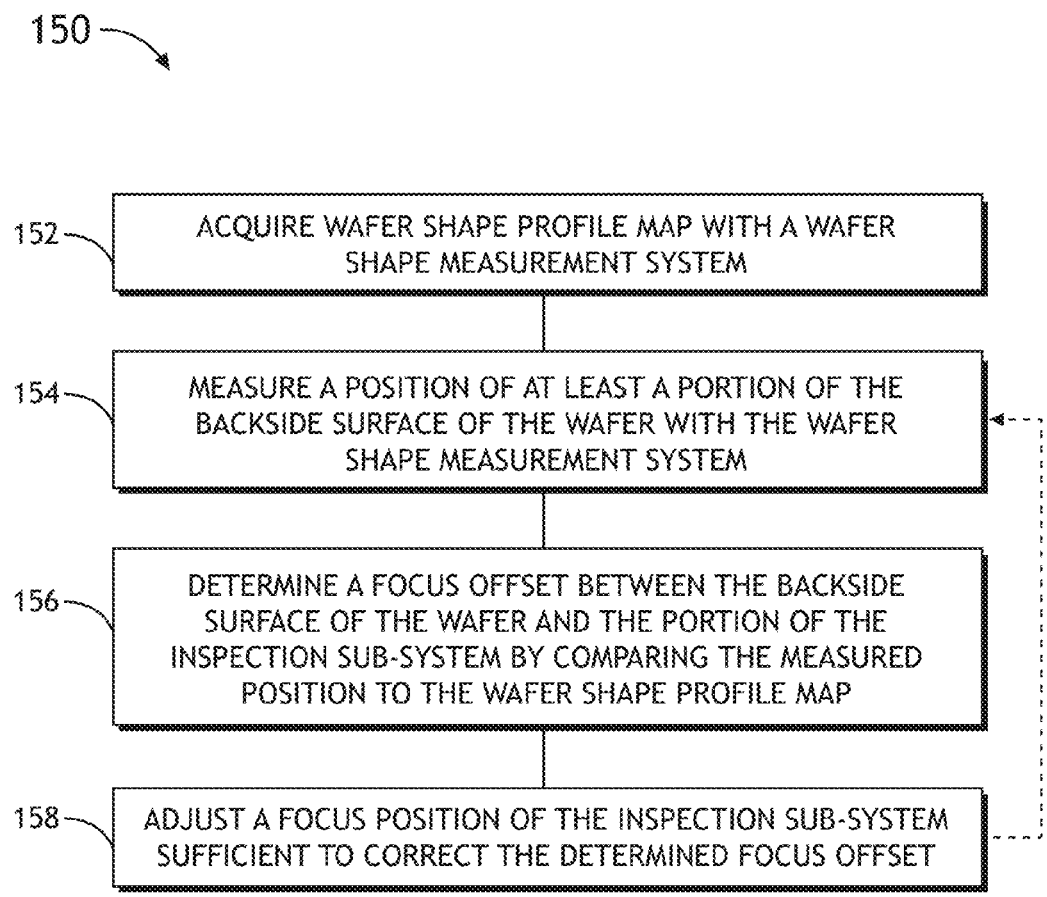
FIG. 1M illustrates a process flow diagram depicting a method for adjusting a focus of a single inspection channel in the multi-channel system, in accordance with one or more embodiments of the present disclosure.

FIG. 1M illustrates a process flow diagram depicting a method 150 for adjusting a focus of a single inspection channel in the multi-channel system, in accordance with one or more embodiments of the present disclosure. In step 152, wafer shape data is acquired with a wafer shape measurement system 140. In one embodiment, the system 100 may perform a pre-scan and/or pre-mapping process on the backside surface 113 of wafer 112 with the one or more wafer measurement systems 140. For example, the pre-scan and/or pre-mapping may be performed when the inspection sub-systems 102a-102e are in a well-focused state prior to a given inspection scan. In one embodiment, one or more wafer shape measurement systems 140 may be used to perform a pre-scan and/or pre-mapping process on the backside surface 113 of wafer 112 in order to acquire one or more wafer profile maps of at least a portion of the wafer 112 corresponding with at least some of the inspection sub-systems 102a-102e. In step 154, the wafer shape measurement system 140 measures a position (e.g., vertical position) of at least a portion of the backside surface 113 of the wafer 112. In step 156, the controller 115 determines a focus offset between the backside surface of the wafer and the portion of the inspection sub-system by comparing the measured position found in step 154 to the wafer shape data acquired in step 152. In this regard, the controller 115 may determine whether a position change has occurred at any point across the wafer 112 and then identify the associated focus offset necessary to compensate for such a change. In step 158, the controller 115 may direct the actuation assembly 108 to adjust a focus position of a respective inspection sub-system 102a-102e sufficient to correct the determined focus offset. In another embodiment, following the focus adjustment of step 158, the measurement step 154 and focus determination step 156 may be repeated as necessary in order to provide further focus adjustments 158, as indicated by the dotted line in FIG. 1M.

Figure 1N:
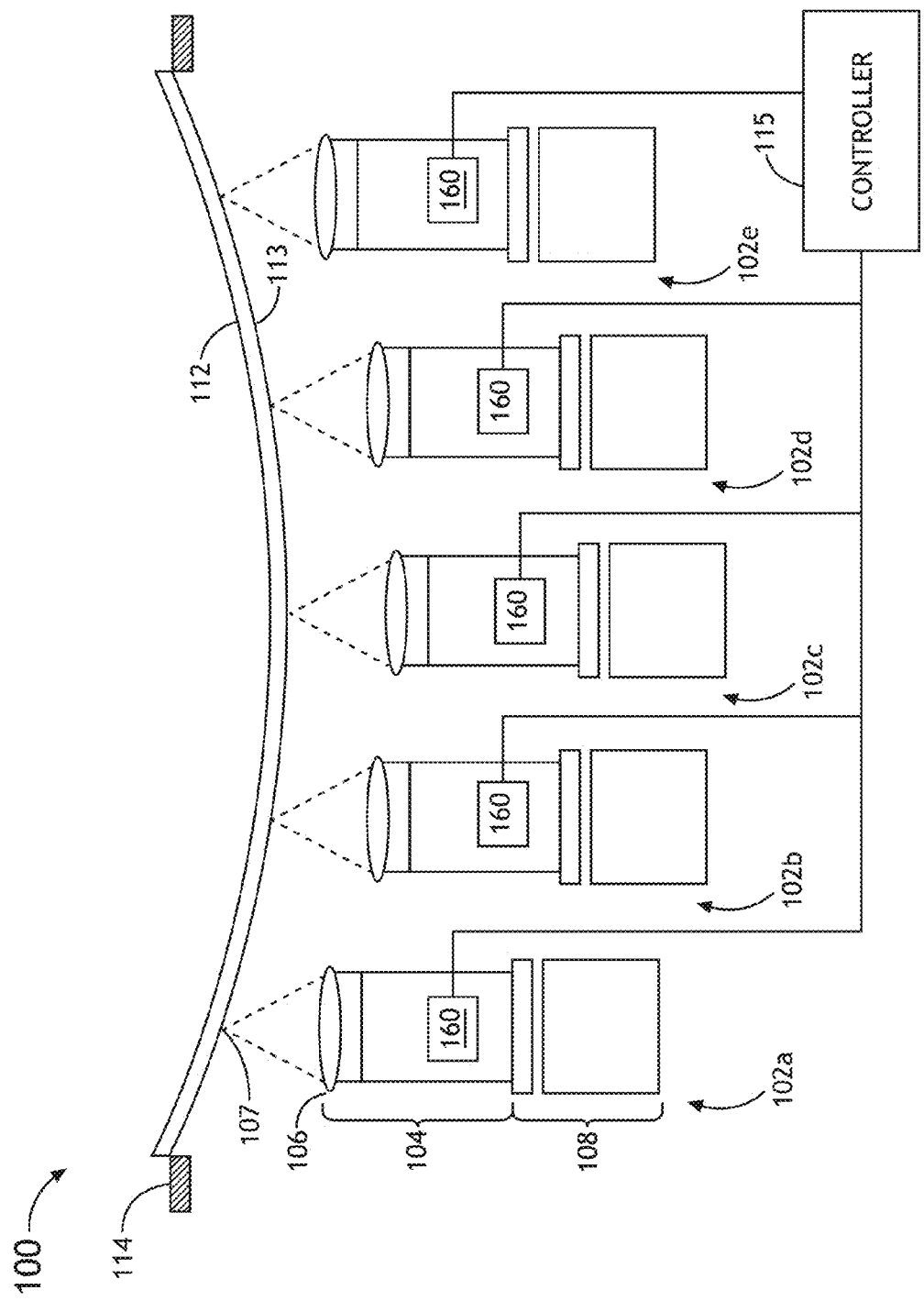
FIG. 1N illustrates a simplified schematic view of a multi-channel inspection system where focus of the individual inspection channels is monitored in real-time with a focus measurement device, in accordance with one or more embodiments of the present disclosure.
Figure 10:
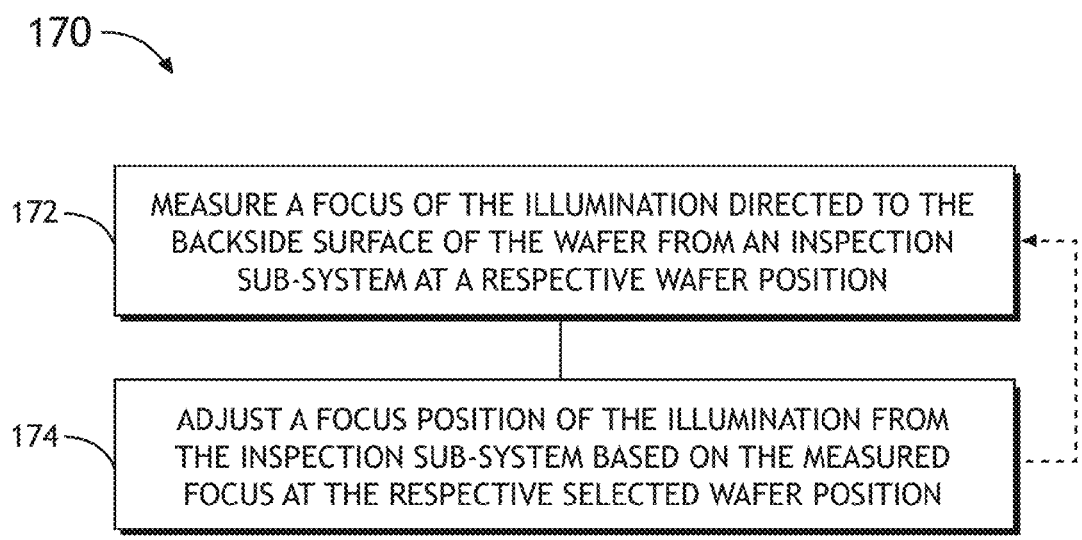

FIG. 1N illustrates a simplified schematic view of a multi-channel inspection system where focus of the individual inspection channels is monitored in real-time with a focus measurement device, in accordance with one or more embodiments of the present disclosure. In one embodiment, the system 100 includes a set of focus measurement devices 160 configured to measure the focus of illumination associated with the respective inspection sub-systems 102a-102e. It is noted herein that the depiction of the focus measurement systems 160 is not limiting and is provided merely for illustrative purposes. It is recognized herein that the system 100 may include any type of focus measurement device known in the art.

In one embodiment, the focus measurement devices 160 are communicatively coupled to the controller 115.

In one embodiment, the controller 115 is configured to acquire measured focus data associated with each of the inspection sub-systems 102a-102e from the focus measurement devices 160. In this regard, each focus measurement device 160 may provide an individual focus measurement for the corresponding inspection sub-system. In another embodiment, the controller 115 may adjust a focus position of one or more of the inspection sub-systems 107 based on the measured focus data from the focus measurement devices 160. For example, the controller 115 may direction a respective actuation assembly 108 to translate the corresponding inspection sub-assembly in order to compensate for any measured focus offset. In this regard, the actuation assembly 108 may make a focus adjustment until the focus 107 of the respective inspection sub-assembly is optimized, or reaches a selected tolerance level.

It is noted herein that the various processes and components described previously herein with respect to FIGS. 1A-1M should be interpreted to extend to the embodiment of FIG. 1N. Further, the processes used to carry out a focus offset procedure should also be interpreted to extend to FIG. 1N.

FIG. 1O illustrates a process flow diagram depicting a method for adjusting a focus of a single inspection channel in the multi-channel system, in accordance with one or more embodiments of the present disclosure. In step 172, a focus measurement device 160 measures a focus of illumination directed to the backside surface of the wafer from a respective inspection sub-system located at respective wafer position. In this regard, the focus measurement systems 160 may measure, independently, the focus 107 of each inspection sub-system 102a-102e. In step 174, the controller 115 may direct the actuation assembly 108 to adjust a focus position of a respective inspection sub-system 102a-102e sufficient to correct for a focus offset measured with the focus measurement systems 160.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A system inspecting a backside surface of a wafer with multi-channel focus control comprising:
   a plurality of inspection sub-systems including a first inspection sub-system positionable at a first wafer position and at least an additional inspection sub-system positionable at an additional wafer position, wherein the wafer is secured at one or more edge portions of the wafer, wherein the backside surface of the wafer is distorted;
   wherein the first inspection sub-system comprises: a first optical assembly; a first actuation assembly, wherein the first optical assembly is disposed on the first actuation assembly; and a first positional sensor configured to sense a position characteristic between a portion of the first optical assembly and the backside surface of the wafer;
   wherein the at least an additional inspection sub-system comprises: at least an additional optical assembly; at least an additional actuation assembly, wherein the at least an additional optical assembly is disposed on the at least an additional actuation assembly; and at least an additional positional sensor configured to sense a position characteristic between a portion of the at least an additional optical assembly and the backside surface of the wafer; and
   a controller, wherein the controller is communicatively coupled to the first actuation assembly, the at least an additional actuation assembly, the first positional sensor and the at least an additional positional sensor, wherein the controller is configured to execute a set of program instructions configured to cause one or more processors to:
   acquire one or more wafer profile maps of the backside surface of the wafer; and
   adjust at least one of a first focus position of the first inspection sub-system or at least an additional focus position of the at least an additional inspection sub-system based on the received one or more wafer profile maps to correct for focus error caused by the distortion of the backside surface of the wafer.

2. The system of claim 1, wherein the acquiring the one or more wafer profile maps comprises:
   performing a pre-mapping process of the backside surface of the wafer in order to generate the one or more wafer profile maps.

3. The system of claim 2, wherein the acquiring the one or more wafer profile maps comprises:
   performing a pre-mapping process of the backside surface of the wafer in order to generate the one or more wafer profile maps with at least one of the first positional sensor or the at least one additional positional sensor.

4. The system of claim 3, wherein the performing a pre-mapping process of the backside surface of the wafer in order to generate the one or more wafer profile maps with at least one of the first positional sensor or the at least one additional positional sensor comprises:
   prior to a selected wafer inspection process, acquiring a plurality of position characteristic values across a plurality of positions of the backside surface of the wafer with at least one of the first positional sensor or the at least one additional positional sensor to scan the backside surface of the wafer; and
   generating the one or more wafer profile maps with the acquired plurality of position characteristic values.

5. The system of claim 2, wherein the acquiring the one or more wafer profile maps comprises:
   prior to a selected wafer inspection process, receiving one or more wafer profile maps of the backside surface of the wafer from a wafer shape measurement system.

6. The system of claim 5, wherein the wafer shape measurement system comprises:
   at least one of an optical-based wafer shape measurement system, a proximity-based wafer shape measurement system, an inductance-based wafer shape measurement system or an air-pressure-based wafer shape measurement system.

7. The system of claim 1, wherein the adjusting at least one of a first focus position of the first inspection sub-system or at least an additional focus position of the at least an additional inspection sub-system based on the received one or more wafer profile maps comprises:
   receiving one or more position characteristic measurements from at least one of the first positional sensor or the at least an additional positional sensor;
   determining a first focus offset between the backside surface of the wafer and the portion of the first optical assembly by comparing the received one or more position characteristic measurement from the first positional sensor to the received one or more wafer profile maps;
   determining an additional focus offset between the backside surface of the wafer and the portion of the at least an additional optical assembly by comparing the received one or more position characteristic measurement from the at least one additional positional sensor to the received one or more wafer profile maps;
   directing the first actuation assembly to adjust the first focus position sufficient to correct the determined first focus offset; and
   directing the at least an additional actuation assembly to adjust the at least an additional focus position sufficient to correct the determined additional focus offset.

8. The system of claim 1, wherein at least of the first optical assembly or the at least an additional optical assembly comprises:
   an illumination source;
   a set of illumination optics including at least an objective configured to focus illumination from the illumination source to a focal point;
   a detector configured to detect illumination reflected or scattered from the wafer; and
   a set of collection optics configured to collect illumination from the surface of the wafer and direct the collected illumination to the detector.

9. The system of claim 1, wherein at least one of the first actuation assembly or the at least an additional actuation assembly comprises:
   an actuation stage;
   an actuator mechanically coupled to the actuation stage and configured to selectively translate the actuation stage.

10. The system of claim 1, wherein the first position sensor and the at least an additional position sensor are located on the same side of the wafer.

11. The system of claim 1, wherein the first position sensor is located on a first side of the wafer and the at least an additional position sensor is located on a second side of the wafer opposite of the first side of the wafer.

12. The system of claim 1, wherein the wafer comprises: a semiconductor wafer.

13. A system for inspecting a backside surface of a wafer with multi-channel focus control comprising:
   a plurality of inspection sub-systems including a first inspection sub-system and at least an additional inspection sub-system, wherein the wafer is secured at one or more edge portions of the wafer, wherein the backside surface of the wafer is distorted,
   wherein the first inspection sub-system comprises: a first optical assembly; and a first actuation assembly, wherein the first optical assembly is disposed on the first actuation assembly;
   wherein the at least an additional inspection sub-system comprises: at least an additional optical assembly; and at least an additional actuation assembly, wherein the at least an additional optical assembly is disposed on the at least an additional actuation assembly;
   a wafer shape measurement system configured to measure a position of at least a portion of the backside surface of the wafer; and
   a controller, wherein the controller is communicatively coupled to the first actuation assembly, the at least an additional actuation assembly, the wafer shape measurement system, wherein the controller is configured to execute a set of program instructions configured to cause one or more processors to:
   acquire wafer shape data from the wafer shape measurement system;
   acquire the measured position of at least a portion of the backside surface of the wafer, from the wafer shape measurement system, at least corresponding with at least one of the first inspection sub-system or the at least an additional inspection sub-system; and
   adjust at least one of a first focus position of the first inspection sub-system or at least an additional focus position of the at least an additional inspection sub-system based on the acquired wafer shape data and the acquired measured position of at least the portion of the backside surface of the wafer to correct for focus error caused by the distortion of the backside surface of the wafer.

14. The system of claim 13, wherein at least of the first optical assembly or the at least an additional optical assembly comprises:
   an illumination source;
   a set of illumination optics including at least an objective configured to focus illumination from the illumination source to a focal point;
   a detector configured to detect illumination reflected or scattered from the wafer; and
   a set of collection optics configured to collect illumination from the surface of the wafer and direct the collected illumination to the detector.

15. The system of claim 13, wherein at least one of the first actuation assembly or the at least an additional actuation assembly comprises:

an actuation stage;
an actuator mechanically coupled to the actuation stage and configured to selectively translate the actuation stage.

16. The system of claim 13, wherein the wafer shape measurement system comprises:
at least one of an optical-based wafer shape measurement system, a proximity-based wafer shape measurement system, an inductance-based wafer shape measurement system or an air-pressure-based wafer shape measurement system.

17. A system for inspecting a backside surface of a wafer with multi-channel focus control comprising:
a plurality of inspection sub-systems including a first inspection sub-system and at least an additional inspection sub-system, wherein the wafer is secured at one or more edge portions of the wafer, wherein the backside surface of the wafer is distorted;
wherein the first inspection sub-system comprises: a first optical assembly; a first actuation assembly, wherein the first optical assembly is disposed on the first actuation assembly; and a first focus measurement device configured to measure the focus of illumination from the first inspection sub-system;
wherein the at least an additional inspection sub-system comprises: at least an additional optical assembly; at least an additional actuation assembly, wherein the at least an additional optical assembly is disposed on the at least an additional actuation assembly; and an additional focus measurement device configured to measure the focus of illumination from the at least an additional inspection sub-system;
a controller, wherein the controller is communicatively coupled to the first actuation assembly, the at least an additional actuation assembly, the first positional sensor and the at least an additional positional sensor, wherein the controller is configured to execute a set of program instructions configured to cause one or more processors to:
receiving a measured first focus of illumination from the first inspection sub-system;
receiving at least an additional focus of illumination from the at least an additional inspection sub-system; and
adjust at least one of a first focus position of the first inspection sub-system or at least an additional focus position of the at least an additional inspection sub-system based on at least one of the measured first focus and the measured at least an additional focus to correct for focus error caused by the distortion of the backside surface of the wafer.

18. The system of claim 17, wherein at least of the first optical assembly or the at least an additional optical assembly comprises:
an illumination source;
a set of illumination optics including at least an objective configured to focus illumination from the illumination source to a focal point;
a detector configured to detect illumination reflected or scattered from the wafer; and
a set of collection optics configured to collect illumination from the surface of the wafer and direct the collected illumination to the detector.

19. The system of claim 17, wherein at least one of the first actuation assembly or the at least an additional actuation assembly comprises:
an actuation stage;
an actuator mechanically coupled to the actuation stage and configured to selectively translate the actuation stage.

20. A method for multi-channel focus control during backside wafer inspection comprising:
acquiring one or more wafer profile maps of the backside surface of the wafer, wherein the wafer is secured at one or more edge portions of the wafer, wherein the backside surface of the wafer is distorted;
measuring a first position characteristic between a portion of a first optical assembly of a first inspection sub-system and the backside surface of the wafer
measuring a second position characteristic between a portion of second optical assembly of a second inspection sub-system and the backside surface of the wafer;
determining a first focus offset between the backside surface of the wafer and the portion of the first optical assembly by comparing the first position characteristic to the received one or more wafer profile maps;
determining a second focus offset between the backside surface of the wafer and the portion of the second optical assembly by comparing the second position characteristic to the received one or more wafer profile maps; and
adjusting a first focus position of the first inspection sub-system sufficient to correct the determined first focus offset caused by the distortion of the backside surface of the wafer; and
adjusting a second focus position of the second inspection sub-system sufficient to correct the determined second focus offset caused by the distortion of the backside surface of the wafer.

21. A method for multi-channel focus control during backside inspection of a wafer comprising:
acquiring wafer shape data at least corresponding with a first wafer position of at least one of the first inspection sub-system or a second wafer position of the at least an additional inspection sub-system, wherein the wafer is secured at one or more edge portions of the wafer, wherein the backside surface of the wafer is distorted;
measuring a first position characteristic between a portion of a first optical assembly of the first inspection sub-system and the backside surface of the wafer;
measuring a second position characteristic between a portion of second optical assembly of the second inspection sub-system and the backside surface of the wafer;
determining a first focus offset between the backside surface of the wafer and the portion of the first optical assembly by comparing the first position characteristic to profile values of the wafer shape data corresponding with the first wafer position;
determining a second focus offset between the backside surface of the wafer and the portion of the second optical assembly by comparing the second position characteristic to profile values of the wafer shape data corresponding with the second wafer position; and
adjust a first focus position of the first inspection sub-system sufficient to correct the determined first focus offset caused by the distortion of the backside surface of the wafer; and
adjust a second focus position of the second inspection sub-system sufficient to correct the determined second focus offset caused by the distortion of the backside surface of the wafer.

22. A method for multi-channel focus control during backside inspection of a wafer comprising:

measuring a first focus of illumination directed to the backside surface of the wafer from a first inspection sub-system located at a first wafer position;

measuring a second focus of illumination directed to the backside surface of the wafer from a second inspection sub-system located at a second wafer position, wherein the wafer is secured at one or more edge portions of the wafer, wherein the backside surface of the wafer is distorted;

adjusting a first focus position of the first inspection sub-system based on the first measured focus at the first wafer position to correct for focus error caused by the distortion of the backside surface of the wafer; and adjusting a second focus position of the second inspection sub-system based on the second measured focus at the second wafer position to correct for focus error caused by the distortion of the backside surface of the wafer.

\* \* \* \* \*

UNITED STATES PATENT AND TRADEMARK OFFICE
CERTIFICATE OF CORRECTION

| | | |
|---|---|---|
| PATENT NO. | : 9,689,804 B2 | Page 1 of 2 |
| APPLICATION NO. | : 14/577374 | |
| DATED | : June 27, 2017 | |
| INVENTOR(S) | : Bobrov | |

It is certified that error appears in the above-identified patent and that said Letters Patent is hereby corrected as shown below:

In the Claims

Column 10, Line 17 Claim 1 should read:
-- A system for inspecting a backside surface of a wafer with --

Column 11, Line 52 Claim 8 should read:
-- The system of claim 1, wherein at least one of the first --

Column 11, Line 67 Claim 9 should read:
-- an actuation stage; and --

Column 12, Line 53 Claim 14 should read:
-- The system of claim 13, wherein at least one of the first --

Column 13, Line 1 Claim 15 should read:
-- an actuation stage; and --

Column 13, Line 67 Claim 19 should read:
-- an actuation stage; and --

Column 14, Line 5 Claim 20 should read:
-- backside inspection of a wafer comprising: --

Column 14, Line 24 Claim 20 should read:
-- the received one or more wafer profile maps; --

Signed and Sealed this
Twelfth Day of September, 2017

Joseph Matal
*Performing the Functions and Duties of the
Under Secretary of Commerce for Intellectual Property and
Director of the United States Patent and Trademark Office*

Column 14, Lines 35-36 Claim 21 should read:
-- acquiring wafer shape data at least corresponding with at least one of a first wafer position of the first inspection --